United States Patent
Gindele et al.

(10) Patent No.: US 9,427,573 B2
(45) Date of Patent: Aug. 30, 2016

(54) DEPLOYABLE ELECTRODE LEAD ANCHOR

(75) Inventors: Paul J. Gindele, Albertville, MN (US); Shiva P. Moosai, New Hope, MN (US); John Jason Buysman, Minnetonka, MN (US); Karen Pilney Montpetit, Mendota Heights, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 988 days.

(21) Appl. No.: 13/167,541

(22) Filed: Jun. 23, 2011

(65) Prior Publication Data

US 2011/0313427 A1 Dec. 22, 2011

Related U.S. Application Data

(63) Continuation-in-part of application No. 12/558,143, filed on Sep. 11, 2009, now abandoned, which is a continuation-in-part of application No. 12/170,582, filed on Jul. 10, 2008, now abandoned.

(Continued)

(51) Int. Cl.
*A61N 1/05* (2006.01)
*A61N 1/36* (2006.01)

(52) U.S. Cl.
CPC ........... *A61N 1/0558* (2013.01); *A61N 1/3606* (2013.01); *A61N 1/36007* (2013.01)

(58) Field of Classification Search
CPC ........... A61N 1/0558; A61N 1/36007; A61N 1/3606
USPC ................................. 607/126–127
See application file for complete search history.

(56) References Cited

U.S. PATENT DOCUMENTS

| 3,628,538 A | 12/1971 | Vincent et al. |
| 3,640,284 A | 2/1972 | De Langis |
| 3,646,940 A | 3/1972 | Timm et al. |
| 3,650,276 A | 3/1972 | Burghele et al. |
| 3,662,758 A | 5/1972 | Glover |
| 3,667,477 A | 6/1972 | Susset et al. |
| 3,866,613 A | 2/1975 | Kenny et al. |
| 3,870,051 A | 3/1975 | Brindley |

(Continued)

FOREIGN PATENT DOCUMENTS

| DE | 8506522.6 U1 | 6/1985 |
| EP | 0245547 A1 | 11/1987 |

(Continued)

OTHER PUBLICATIONS

Prosecution Documents associated with U.S. Appl. No. 12/558,143 including: Office Action mailed Dec. 13, 2011; Office Action mailed Sep. 29, 2011; and Office Action mailed Jun. 20, 2011.

(Continued)

*Primary Examiner* — Rex R Holmes
(74) *Attorney, Agent, or Firm* — Westman, Champlin & Koehler, P.A.

(57) ABSTRACT

One embodiment of an electrode lead comprises a lead body, at least one electrode at a distal end of the lead body, an actuatable member and at least one anchor wire. The actuatable member is positioned within a lumen of the lead body. The at least one anchor wire has a proximal end that is attached to the actuatable member. Movement of the actuatable member relative to the lead body moves the at least one anchor wire through at least one opening in the lead body.

16 Claims, 9 Drawing Sheets

Related U.S. Application Data

(60) Provisional application No. 61/358,053, filed on Jun. 24, 2010, provisional application No. 61/360,157, filed on Jun. 30, 2010, provisional application No. 61/096,387, filed on Sep. 12, 2008, provisional application No. 61/160,765, filed on Mar. 17, 2009, provisional application No. 60/948,908, filed on Jul. 10, 2007.

(56) References Cited

U.S. PATENT DOCUMENTS

| | | |
|---|---|---|
| 3,926,178 A | 12/1975 | Feldzamen |
| 3,941,136 A | 3/1976 | Bucalo |
| 3,983,865 A | 10/1976 | Shepard |
| 3,983,881 A | 10/1976 | Wickham |
| 4,010,758 A | 3/1977 | Rockland et al. |
| 4,023,574 A | 5/1977 | Nemec |
| 4,030,509 A | 6/1977 | Heilman et al. |
| 4,044,774 A | 8/1977 | Corbin et al. |
| 4,106,511 A | 8/1978 | Erlandsson |
| 4,136,684 A | 1/1979 | Scattergood et al. |
| 4,139,006 A | 2/1979 | Corey |
| 4,153,059 A | 5/1979 | Fravel et al. |
| 4,157,087 A | 6/1979 | Miller et al. |
| 4,165,750 A | 8/1979 | Aleev et al. |
| 4,177,819 A | 12/1979 | Kofsky et al. |
| 4,222,377 A | 9/1980 | Burton |
| 4,290,420 A | 9/1981 | Manetta |
| 4,387,719 A | 6/1983 | Plevnik et al. |
| 4,402,328 A | 9/1983 | Doring |
| 4,406,288 A | 9/1983 | Horwinski et al. |
| 4,414,986 A | 11/1983 | Dickhudt et al. |
| 4,431,001 A | 2/1984 | Hakansson et al. |
| 4,457,299 A | 7/1984 | Cornwell |
| 4,492,233 A | 1/1985 | Petrofsky et al. |
| 4,515,167 A | 5/1985 | Hochman |
| 4,542,753 A | 9/1985 | Brenman et al. |
| 4,568,339 A | 2/1986 | Steer |
| 4,569,351 A | 2/1986 | Tang |
| 4,571,749 A | 2/1986 | Fischell |
| 4,580,578 A | 4/1986 | Barsom |
| 4,585,005 A | 4/1986 | Lue et al. |
| 4,602,624 A | 7/1986 | Naples et al. |
| 4,607,639 A | 8/1986 | Tanagho et al. |
| 4,628,942 A | 12/1986 | Sweeney et al. |
| 4,688,575 A | 8/1987 | DuVall |
| 4,703,755 A | 11/1987 | Tanagho et al. |
| 4,731,083 A | 3/1988 | Fischell |
| 4,739,764 A | 4/1988 | Lue et al. |
| 4,750,494 A | 6/1988 | King |
| 4,771,779 A | 9/1988 | Tanagho et al. |
| 4,785,828 A | 11/1988 | Maurer |
| 4,881,526 A | 11/1989 | Johnson et al. |
| 4,913,164 A | 4/1990 | Greene et al. |
| 4,941,874 A | 7/1990 | Sandow et al. |
| 5,013,292 A | 5/1991 | Lemay |
| 5,019,032 A | 5/1991 | Robertson |
| 5,082,006 A | 1/1992 | Jonasson |
| 5,094,242 A | 3/1992 | Gleason et al. |
| 5,103,835 A | 4/1992 | Yamada et al. |
| 5,112,344 A | 5/1992 | Petros |
| 5,193,539 A | 3/1993 | Schulman et al. |
| 5,193,540 A | 3/1993 | Schulman et al. |
| 5,199,430 A | 4/1993 | Fang et al. |
| 5,285,781 A | 2/1994 | Brodard |
| 5,291,902 A | 3/1994 | Carman |
| 5,312,439 A | 5/1994 | Loeb |
| 5,324,316 A | 6/1994 | Schulman et al. |
| 5,324,324 A | 6/1994 | Vachon et al. |
| 5,330,507 A | 7/1994 | Schwartz |
| 5,358,514 A | 10/1994 | Schulman et al. |
| 5,405,367 A | 4/1995 | Schulman et al. |
| 5,411,548 A | 5/1995 | Carman |
| 5,417,226 A | 5/1995 | Juma |
| 5,423,329 A | 6/1995 | Ergas |
| 5,452,719 A | 9/1995 | Eisman et al. |
| 5,484,445 A | 1/1996 | Knuth |
| 5,518,504 A | 5/1996 | Polyak |
| 5,520,606 A | 5/1996 | Schoolman et al. |
| 5,562,717 A | 10/1996 | Tippey et al. |
| 5,569,351 A | 10/1996 | Menta et al. |
| 5,571,148 A | 11/1996 | Loeb et al. |
| 5,611,515 A | 3/1997 | Benderev et al. |
| 5,611,768 A | 3/1997 | Tutrone, Jr. |
| 5,634,462 A | 6/1997 | Tyler et al. |
| 5,702,428 A | 12/1997 | Tippey et al. |
| 5,752,978 A | 5/1998 | Chancellor |
| 5,807,397 A | 9/1998 | Barreras |
| 5,824,027 A | 10/1998 | Hoffer et al. |
| 5,833,595 A | 11/1998 | Lin |
| 5,842,478 A | 12/1998 | Benderev et al. |
| 5,860,425 A | 1/1999 | Benderev et al. |
| 5,899,909 A | 5/1999 | Claren et al. |
| 5,927,282 A | 7/1999 | Lenker et al. |
| 5,931,864 A | 8/1999 | Chastain et al. |
| 5,954,761 A | 9/1999 | Machek et al. |
| 5,957,920 A | 9/1999 | Baker |
| 5,957,965 A | 9/1999 | Moumane et al. |
| 5,978,712 A | 11/1999 | Suda et al. |
| 5,984,854 A | 11/1999 | Ishikawa et al. |
| 6,002,964 A | 12/1999 | Feler et al. |
| 6,026,326 A | 2/2000 | Bardy |
| 6,027,456 A | 2/2000 | Feler et al. |
| 6,039,686 A | 3/2000 | Kovac |
| 6,042,534 A | 3/2000 | Gellman et al. |
| 6,051,017 A | 4/2000 | Loeb et al. |
| 6,055,456 A | 4/2000 | Gerber |
| 6,061,596 A | 5/2000 | Richmond et al. |
| 6,104,955 A | 8/2000 | Bourgeois |
| 6,104,960 A | 8/2000 | Duysens et al. |
| 6,110,101 A | 8/2000 | Tihon et al. |
| 6,131,575 A | 10/2000 | Lenker et al. |
| 6,135,945 A | 10/2000 | Sultan |
| 6,141,594 A | 10/2000 | Flynn et al. |
| 6,161,029 A | 12/2000 | Spreigl et al. |
| 6,178,356 B1 | 1/2001 | Chastain et al. |
| 6,185,452 B1 | 2/2001 | Schulman et al. |
| 6,208,894 B1 | 3/2001 | Schulman et al. |
| 6,240,315 B1 | 5/2001 | Mo et al. |
| 6,240,316 B1 | 5/2001 | Richmond et al. |
| 6,243,607 B1 | 6/2001 | Mintchev et al. |
| 6,266,557 B1 | 7/2001 | Roe et al. |
| 6,266,564 B1 | 7/2001 | Hill et al. |
| 6,304,786 B1 | 10/2001 | Heil et al. |
| 6,328,686 B1 | 12/2001 | Kovac |
| 6,341,236 B1 | 1/2002 | Osorio et al. |
| 6,354,991 B1 | 3/2002 | Gross et al. |
| 6,360,750 B1 | 3/2002 | Gerber et al. |
| 6,366,814 B1 | 4/2002 | Boveja et al. |
| 6,382,214 B1 | 5/2002 | Raz et al. |
| 6,397,109 B1 | 5/2002 | Cammilli et al. |
| 6,407,308 B1 | 6/2002 | Roe et al. |
| 6,418,930 B1 | 7/2002 | Fowler |
| 6,505,082 B1 | 1/2003 | Scheiner et al. |
| 6,582,441 B1 | 6/2003 | He et al. |
| 6,600,956 B2 | 7/2003 | Maschino et al. |
| 6,612,977 B2 | 9/2003 | Staskin et al. |
| 6,641,524 B2 | 11/2003 | Kovac |
| 6,650,943 B1 | 11/2003 | Whitehurst et al. |
| 6,652,449 B1 | 11/2003 | Gross et al. |
| 6,652,450 B2 | 11/2003 | Neisz et al. |
| 6,652,499 B1 | 11/2003 | Edgren et al. |
| 6,658,297 B2 | 12/2003 | Loeb |
| 6,659,936 B1 | 12/2003 | Furness et al. |
| 6,662,045 B2 * | 12/2003 | Zheng et al. ............ 607/5 |
| 6,712,772 B2 | 3/2004 | Cohen et al. |
| 6,735,474 B1 | 5/2004 | Loeb et al. |
| 6,745,079 B2 | 6/2004 | King |
| 6,802,807 B2 | 10/2004 | Anderson et al. |
| 6,862,480 B2 | 3/2005 | Cohen et al. |
| 6,896,651 B2 | 5/2005 | Gross et al. |
| 6,911,003 B2 | 6/2005 | Anderson et al. |
| 6,941,171 B2 | 9/2005 | Mann et al. |
| 6,952,613 B2 | 10/2005 | Swoyer et al. |

(56) References Cited

U.S. PATENT DOCUMENTS

| | | | |
|---|---|---|---|
| 6,964,643 B2 | 11/2005 | Hovland et al. | |
| 6,964,699 B1 | 11/2005 | Carns et al. | |
| 6,971,393 B1 | 12/2005 | Mamo et al. | |
| 7,079,882 B1 | 7/2006 | Schmidt | |
| 7,120,499 B2 | 10/2006 | Thrope et al. | |
| 7,319,905 B1 | 1/2008 | Morgan et al. | |
| 7,328,068 B2 | 2/2008 | Spinelli et al. | |
| 7,330,764 B2 | 2/2008 | Swoyer et al. | |
| 7,343,202 B2 | 3/2008 | Mrva et al. | |
| 7,376,467 B2 | 5/2008 | Thrope et al. | |
| 7,613,516 B2 | 11/2009 | Cohen et al. | |
| 7,628,795 B2 | 12/2009 | Karwoski et al. | |
| 7,647,113 B2 | 1/2010 | Wirbisky et al. | |
| 7,771,345 B1 | 8/2010 | O'Donnell | |
| 2001/0002441 A1 | 5/2001 | Boveja | |
| 2001/0003799 A1 | 6/2001 | Boveja | |
| 2001/0018549 A1 | 8/2001 | Scetbon | |
| 2002/0055761 A1 | 5/2002 | Mann et al. | |
| 2002/0099259 A1 | 7/2002 | Anderson et al. | |
| 2002/0161382 A1 | 10/2002 | Neisz et al. | |
| 2002/0161423 A1* | 10/2002 | Lokhoff et al. | 607/127 |
| 2002/0165566 A1 | 11/2002 | Ulmsten | |
| 2003/0018365 A1 | 1/2003 | Loeb | |
| 2003/0023296 A1 | 1/2003 | Osypka | |
| 2003/0028232 A1 | 2/2003 | Camps et al. | |
| 2003/0060868 A1 | 3/2003 | Janke et al. | |
| 2003/0100930 A1 | 5/2003 | Cohen et al. | |
| 2003/0171644 A1 | 9/2003 | Anderson et al. | |
| 2003/0199961 A1 | 10/2003 | Bjorklund et al. | |
| 2003/0236557 A1 | 12/2003 | Whitehurst et al. | |
| 2003/0236558 A1 | 12/2003 | Whitehurst et al. | |
| 2004/0015057 A1 | 1/2004 | Rocheleau et al. | |
| 2004/0015204 A1 | 1/2004 | Whitehurst et al. | |
| 2004/0015205 A1 | 1/2004 | Whitehurst et al. | |
| 2004/0039453 A1 | 2/2004 | Anderson et al. | |
| 2004/0059392 A1 | 3/2004 | Parramon et al. | |
| 2004/0068203 A1 | 4/2004 | Gellman et al. | |
| 2004/0093053 A1 | 5/2004 | Gerber et al. | |
| 2004/0242956 A1 | 12/2004 | Scorvo | |
| 2004/0248979 A1 | 12/2004 | Brettman et al. | |
| 2005/0038489 A1 | 2/2005 | Grill | |
| 2005/0043580 A1 | 2/2005 | Watschke et al. | |
| 2005/0065395 A1 | 3/2005 | Mellier | |
| 2005/0113877 A1 | 5/2005 | Spinelli et al. | |
| 2005/0119710 A1 | 6/2005 | Furness et al. | |
| 2005/0143618 A1 | 6/2005 | Anderson et al. | |
| 2005/0149156 A1 | 7/2005 | Libbus et al. | |
| 2005/0216069 A1 | 9/2005 | Cohen et al. | |
| 2005/0228346 A1 | 10/2005 | Goode et al. | |
| 2005/0245787 A1 | 11/2005 | Cox et al. | |
| 2005/0245874 A1 | 11/2005 | Carrez et al. | |
| 2005/0250977 A1 | 11/2005 | Montpetit et al. | |
| 2005/0251240 A1* | 11/2005 | Doan | 607/127 |
| 2005/0283235 A1 | 12/2005 | Kugler et al. | |
| 2006/0004421 A1 | 1/2006 | Bennett et al. | |
| 2006/0004429 A1 | 1/2006 | Mrva et al. | |
| 2006/0149345 A1 | 7/2006 | Boggs, II et al. | |
| 2006/0241733 A1 | 10/2006 | Zhang et al. | |
| 2006/0287571 A1 | 12/2006 | Gozzi et al. | |
| 2007/0021650 A1 | 1/2007 | Rocheleau et al. | |
| 2007/0043416 A1 | 2/2007 | Callas et al. | |
| 2007/0123952 A1 | 5/2007 | Strother et al. | |
| 2007/0156219 A1* | 7/2007 | Sommer et al. | 607/131 |
| 2007/0179559 A1 | 8/2007 | Giftakis et al. | |
| 2007/0185541 A1 | 8/2007 | DiUbaldi et al. | |
| 2007/0239224 A1 | 10/2007 | Bennett et al. | |
| 2007/0253997 A1 | 11/2007 | Giftakis et al. | |
| 2007/0253998 A1 | 11/2007 | Giftakis et al. | |
| 2007/0255333 A1 | 11/2007 | Giftakis et al. | |
| 2007/0255341 A1 | 11/2007 | Giftakis et al. | |
| 2007/0260288 A1 | 11/2007 | Gross et al. | |
| 2007/0265675 A1 | 11/2007 | Lund et al. | |
| 2008/0009914 A1 | 1/2008 | Buysman et al. | |
| 2008/0071321 A1 | 3/2008 | Boggs, II et al. | |
| 2008/0132969 A1 | 6/2008 | Bennett et al. | |
| 2009/0012592 A1 | 1/2009 | Buysman | |
| 2009/0043356 A1 | 2/2009 | Longhini et al. | |
| 2009/0157091 A1 | 6/2009 | Buysman | |
| 2010/0049289 A1 | 2/2010 | Lund et al. | |
| 2010/0076254 A1 | 3/2010 | Jimenez et al. | |
| 2012/0095478 A1 | 4/2012 | Wang et al. | |

FOREIGN PATENT DOCUMENTS

| | | |
|---|---|---|
| EP | 1 661 600 A1 | 5/2006 |
| EP | 1119314 B1 | 6/2006 |
| EP | 2295109 A2 | 3/2011 |
| GB | 2309388 | 7/1997 |
| WO | 9012617 A1 | 11/1990 |
| WO | 9604955 A2 | 2/1996 |
| WO | 9632916 A1 | 10/1996 |
| WO | 9817190 A2 | 4/1998 |
| WO | 0000082 A1 | 1/2000 |
| WO | 0019940 A1 | 4/2000 |
| WO | 0239890 A2 | 5/2002 |
| WO | 02069781 A2 | 9/2002 |
| WO | 02078592 A2 | 10/2002 |
| WO | 03002192 A1 | 1/2003 |
| WO | 2006047833 A1 | 5/2006 |
| WO | 2007097994 A2 | 8/2007 |
| WO | 2007126632 A3 | 11/2007 |
| WO | 2007145913 A1 | 12/2007 |
| WO | 2009017680 A2 | 2/2009 |
| WO | 2009075800 A1 | 6/2009 |
| WO | 2010107751 A2 | 9/2010 |

OTHER PUBLICATIONS

Yamanishi et al., "Electrical Stimulation for Stress Incontinence", Int. Urogynecol J (1998) 9:281-290 Springer-Verlag London Ltd.
International Search Report and Written Opinion dated Apr. 21, 2011 from International Application No. PCT/US2011/023677, filed Feb. 4, 2011.
Dietz et al., "Mechanical Properties of Urogynecologic Implant Materials", Int. Urogynecol J. (2003) 14:239-243.
Iglesia et al., "The Use of Mesh in Gynecologic Surgery", Int. Urogynecol J. (1997) 8:105-115.
Partial European Search Report from European Patent Application No. 10176162.5, mailed Jan. 21, 2011.
European Search Report and Written Opinion of 06011641.5, mailed Aug. 21, 2006.
International Search Report and Written Opinion of PCT/US2007/004474, filed Feb. 22, 2007.
International Search Report and Written Opinion of PCT/US2007/000112, filed Jan. 3, 2007.
U.S. Appl. No. 12/406,434, filed Mar. 18, 2009.
Caldwell, K.P.S. et al. "Urethral Pressure Recordings in Male Incontinents Under Electrical Stimulation." Investigative Urology vol. 5, No. 6, pp. 572-579, May 1968.
Caldwell, K.P.S. et al. "Stress Incontinence in Females: Report on 31 Cases Treated by Electrical Implant." J. Obstet. Gynaec. Brit. Cwlth vol. 75, pp. 777-780, Jul. 1968.
Caldwell, K.P.S. "Electrical Stimulation.", Sphincter Research Unit, Royal Devon and Exeter Hospital, Exeter (England), Urol. Int. 29: 225, 1974. (1 page).
Caldwell, K.P.S. "The Use of Electrical Stimulation in Urinary Retention and Incontinence [Abridged]." Section of Urology, vol. 61, pp. 35-39, Jul. 1968.
Notification of the First Office Action from Chinese patent application No. 200780007709.2, mailed Sep. 27, 2010.
Extended European Search Report and Opinion for European patent application No. 10176162.5, dated Apr. 28, 2011.
Yamamoto et al., "Optimal parameters for effective electrical stimulation of the anal sphincters in a child with fecal incontinence: preliminary report," Pediatr Surg Int (1993) 8:132-137.

* cited by examiner

DEPLOYABLE ELECTRODE LEAD ANCHOR

CROSS-REFERENCE TO RELATED APPLICATION

The present application is based on and claims the benefit of U.S. provisional patent application Ser. No. 61/358,053, filed Jun. 24, 2010, and U.S. provisional patent application Ser. No. 61/360,157, filed Jun. 30, 2010. The present application is a continuation-in-part of and claims priority to U.S. patent application Ser. No. 12/558,143, filed Sep. 11, 2009, now abandoned, which claims the benefit of U.S. provisional patent application Ser. Nos. 61/096,387 filed Sep. 12, 2008 and 61/160,765 filed Mar. 17, 2009, and is a continuation-in-part of U.S. application Ser. No. 12/170,582 filed Jul. 10, 2008, now abandoned, which in turn claims the benefit of U.S. provisional patent application Ser. No. 60/948,908, filed Jul. 10, 2007. The content of each of the above-referenced applications is hereby incorporated by reference in their entirety.

FIELD

Embodiments of the invention generally relate to a deployable anchor that facilitates securing an electrode lead to internal tissue of a patient and preventing migration of the electrode lead relative to the tissue of the patient. Embodiments of the anchor may also be retracted to simplify the removal of the electrode lead from the tissue of the patient.

BACKGROUND

Implantable electronic stimulator devices, such as neuromuscular stimulation devices, have been disclosed for use in the treatment of various pelvic conditions, such as urinary incontinence, fecal incontinence and sexual dysfunction. Such devices generally include one or more electrodes that are coupled to a control unit by electrode leads. Electrical signals are applied to the desired pelvic tissue of the patient through the electrode leads in order to treat the condition of the patient. The electrode leads are typically secured to the tissue using an anchor in the form of a helical coil. Exemplary implantable electronic stimulator devices and uses of the devices are disclosed in U.S. Pat. Nos. 6,354,991, 6,652,449, 6,712,772 and 6,862,480, each of which is hereby incorporated by reference in its entirety.

An anchor is typically attached to the distal end of the electrode lead to secure the electrode lead within tissue of the patient and prevent relative movement between the anchor and the tissue in which the anchor in embedded.

SUMMARY

Some embodiments of the invention are directed to an electrode lead comprising a lead body, at least one electrode at a distal end of the lead body, an actuatable member and at least one anchor wire. The actuatable member is positioned within a lumen of the lead body. The at least one anchor wire has a proximal end that is attached to the actuatable member. Movement of the actuatable member relative to the lead body moves the at least one anchor wire through at least one opening in the lead body.

Another embodiment is directed to a system that comprises an introducer sheath, an electrode lead and at least one anchor wire. The introducer sheath has a sheath wall and a longitudinal axis. The electrode lead comprises a lead body and at least one electrode at a distal end of the lead body. The distal end of a lead body is received within the sheath. The at least one anchor wire has a proximal end that is attached to the distal end of the lead body. The at least one anchor wire moves through at least one opening in the sheath wall responsive to movement of the lead body relative to the introducer sheath.

Yet another embodiment is directed to a method. In the method, an electrode lead is provided. In on embodiment, the electrode lead comprises a lead body, at least one electrode at a distal end of lead body and at least one anchor wire having a proximal end connected to the lead body. The distal end of the lead body is positioned within tissue of a patient. The distal end of the at least one anchor wire is moved radially from the lead body and into the tissue to anchor the distal end of the lead body to the tissue.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Embodiments of the invention are directed to an anchor that facilitates securing an electrode lead to internal tissue of a patient to prevent migration of the electrode lead from its intended position. The tissue in which the anchors of the present invention may be used includes adipose tissue, muscle tissue or any other tissue of the patient. In one embodiment, the tissue is located in the pelvic region of the patient. In some embodiments, the tissue, in which the anchor is to be embedded, is targeted for electrical stimulation or is adjacent a desired stimulation target site. Embodiments of the invention comprise the individual embodiments described below and combinations of two or more of the embodiments described below. Elements having the same or similar labels correspond to the same or similar elements.

Figure 1:
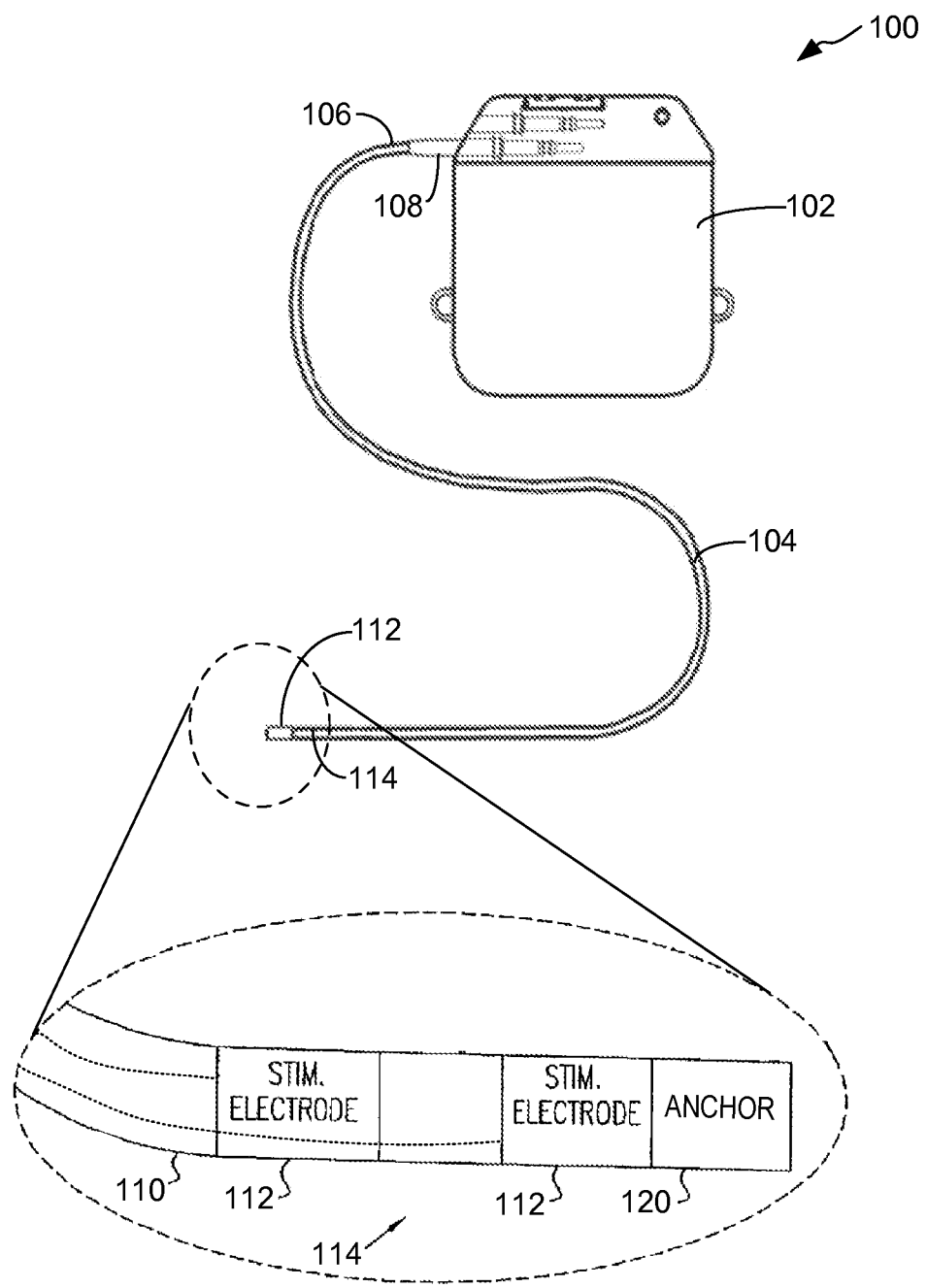
FIG. 1 is a side plan view of an exemplary electronic stimulator device, in accordance with the embodiments of the invention.

FIG. 1 is a side plan view of an exemplary electronic stimulator system 100, with which embodiments of the anchors of the present invention may be used. System 100 is configured for implantation into a pelvic region of a patient to provide muscle and/or nerve stimulation that is used to control and/or treat a pelvic condition of the patient, such as pelvic pain, urinary incontinence, fecal incontinence, erectile dysfunction or other pelvic condition that may be treated through electrical stimulation.

In one embodiment, the system 100 comprises a control unit 102 and one or more electrode leads 104, a proximal end 106 of which is coupled to the control unit 102 via a connector 108. Each electrode lead 104 comprises a lead body 110 and one or more stimulating electrodes 112 at a distal end 114 of the electrode lead 104 or lead body 110. The lead body 110 insulates electrical wires connecting the control unit 102 to the stimulating electrodes 112. The lead body 110 can be in the form of an insulating jacket typically comprising silicone, polyurethane or other flexible, biocompatible electrically insulating material. Additional electrode leads 104 or physiological sensors may be coupled to the control unit 102.

In one embodiment, the control unit 102 comprises circuitry for processing electrical signals received from the one or more stimulating electrodes 112 or physiological sensors. The control unit 102 is also configured to apply an electrical current or waveform to the tissue of the patient that is in contact with the one or more stimulating electrodes 112.

The electrode lead 104 can be anchored to pelvic tissue of the patient (e.g., internal urinary sphincter muscle) by means of a tissue anchor 120, which is formed in accordance with embodiments of the invention described below. The anchor 120 operates to secure the position of the distal end 114 of the electrode lead 104 in the desired tissue of the patient. In one embodiment, the anchor 120 is located at the distal end 114 proximate the one or more electrodes 112. While depicted as being located at the terminating side of the electrodes 112, the anchor 120 may be located between electrodes 112 or between the electrodes 112 and the proximal end 106 of the electrode lead.

Figure 2:
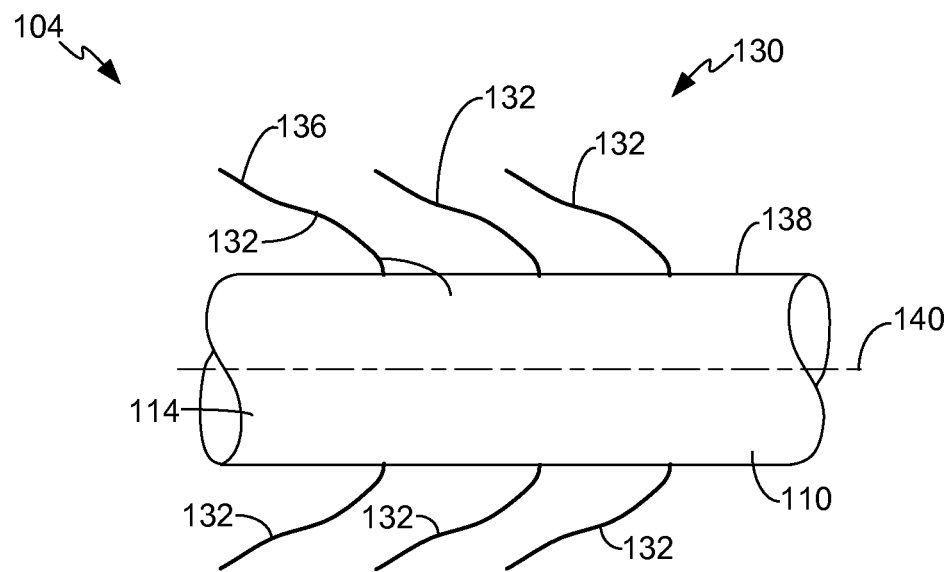
FIGS. 2 and 3 are simplified side views of a portion of an electrode lead illustrating anchors formed in accordance with embodiments of the invention.

FIG. 2 is simplified side view of a portion of a distal end 114 of electrode lead 104 that includes an anchor 130 in accordance with embodiments of the invention. The anchor 130 comprises at least one anchor wire 132 having a proximal end 134 that is attached to the lead body 110. A distal end 136 of each anchor wire 132 is configured to be fed into tissue of a patient to secure the distal end 114 of the electrode lead 104 to the tissue.

The one or more anchor wires 132 are generally formed of a suitable biocompatible material. In one embodiment, the anchor wires 132 are flexible, yet firm enough to pierce tissue of the patient upon deployment, as described below. In one embodiment, the wires 132 are formed of a memory shaped material, such as nickel titanium (i.e., NITINOL), that forces each of the anchor wires 132 to follow a desired trajectory as the wires 132 are deployed into the tissue of the patient, for example.

In one embodiment, the anchor wires 132 are attached to a sidewall 138 of the lead body 110. In one embodiment, each of the anchor wires 132 is displaced from adjacent anchor wires 132 along a longitudinal axis 140 of the lead body 110. In accordance with another embodiment, the anchor wires 132 are angularly displaced from each other about the longitudinal axis 140. For instance, the anchor wires 132 may be angularly displaced by 90 degrees from each other, as shown in FIG. 2, or other angular displacement.

Figure 3:
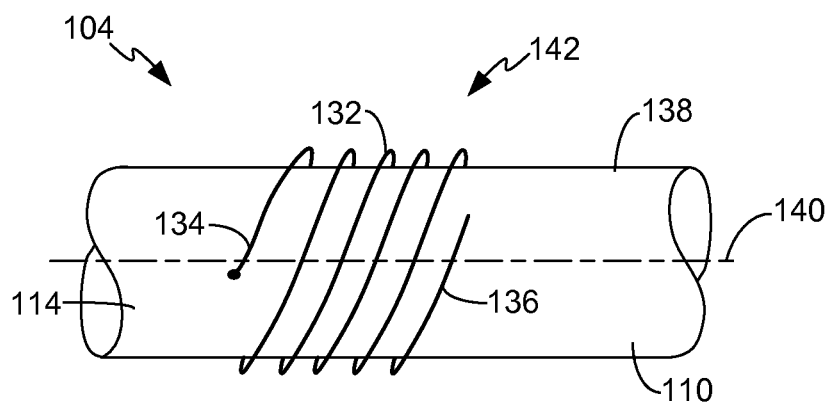

FIG. 3 is a simplified side view of a distal end 114 of an electrode lead 104 that includes an anchor 142 in accordance with embodiments of the invention. One embodiment of the anchor 142 comprises a least one anchor wire 132 having a proximal end 134 as attached to a side wall 138 of the lead body 110. In one embodiment, the anchor wire 132 is initially wrapped around the lead body 110 and the axis 140 in a coil. In one embodiment, the anchor 142 includes a plurality of anchor wires 132 that are coiled around the lead body 110. This embodiment is not illustrated in order to simplify the drawing.

Figure 4:
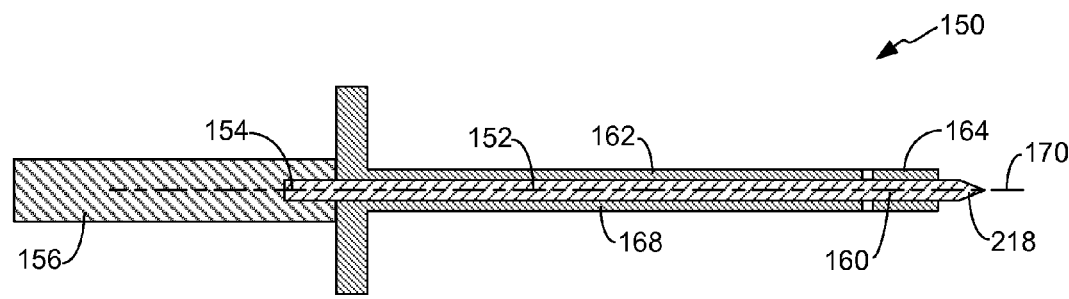
FIG. 4 is a simplified side cross-sectional view of an exemplary introducer in accordance with embodiments of the invention.

In one embodiment, the distal ends 114 of the electrode leads 104 illustrated in FIGS. 2 and 3 are configured to be deployed into tissue of a patient using an introducer. A simplified side cross-sectional view of an exemplary introducer 150 that may be used to deploy the electrode leads 104 of FIGS. 2 and 3 is provided in FIG. 4. In one embodiment, the introducer 150 is formed of biocompatible materials. A guide needle 152 having a proximal end 154 coupled to a handle 156 and a needle tip 158 at a distal end 160 may be received within an introducer sheath 162 of the introducer 150. The combination of the guide needle 152 and the introducer sheath 162 is used by the physician to create a pathway to the tissue of the patient that is targeted for electrical stimulation. Once the needle tip 158 of the guide needle 152 is positioned in or adjacent to the targeted tissue, the guide needle 152 is removed from the introducer sheath 162. This creates a pathway through the patient to the targeted tissue. The distal end 114 of the electrode lead 104 may then be inserted through the introducer sheath 162 to place the distal end 114 of the electrode lead 104 at the distal end 164 of the introducer sheath 162, in accordance with conventional techniques.

Figure 5:
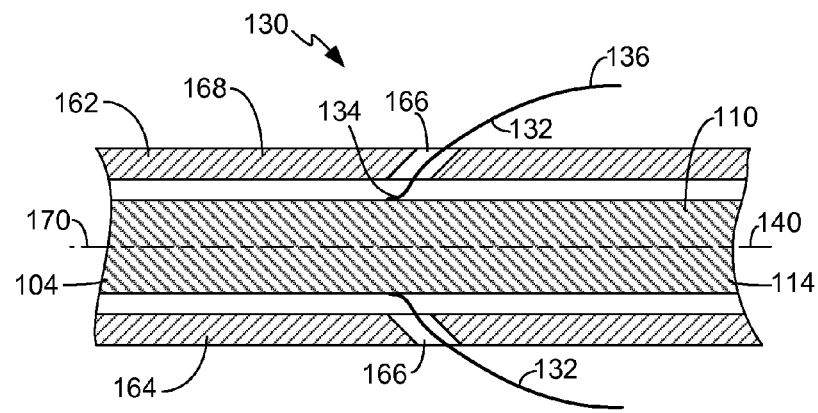
FIG. 5 is a simplified side cross-sectional view of a portion of the electrode lead of FIG. 2 within an introducer sheath.

FIG. 5 illustrates a portion of the distal end 114 of the electrode lead 104 of FIG. 2 within the distal end 164 of the introducer sheath 162. In one embodiment, the distal end 164 of the introducer sheath 162 includes at least one opening 166 in a sheath wall 168. The one or more openings 166 are configured to receive the distal ends 136 of corresponding anchor wires 132 of the anchor 130. As the distal end 114 of the electrode lead 104 is advanced toward the distal end 164 of the introducer sheath by the physician along a longitudinal axis 170 of the introducer sheath, which generally corresponds to the axis 140 of the lead body 110, the distal ends 136 of the one or more anchor wires 132 travel through to the corresponding openings 166 in the sheath wall 168, as shown in FIG. 5. Continued motion of the distal end 114 of the electrode lead 104 relative to the introducer sheath 162 causes the distal ends 136 to extend into the tissue of the patient. In one embodiment, the anchor wire 132 travels in the direction that is generally radial to the longitudinal axis 170 of the introducer sheath 162 and/or the longitudinal axis 140 of the lead body 110.

This deployment of the one or more anchor wires 132 of the anchor 130 is followed by the removal of the introducer sheath 162 in accordance with conventional techniques. For instance, the introducer sheath 162 may be split into separate halves that allow for the removal of the introducer sheath 162 without disrupting the placement of the anchor wires 132 in the tissue of the patient. The one or more anchor wires 132 that extend generally radially from the longitudinal axis 140 of the lead body 110 into the tissue of the patient operate to secure the position of the distal end 114 in the targeted tissue. The electrode lead 104 may then be used to perform electrical stimulation operations on the targeted tissue in accordance with conventional techniques.

Figure 6:
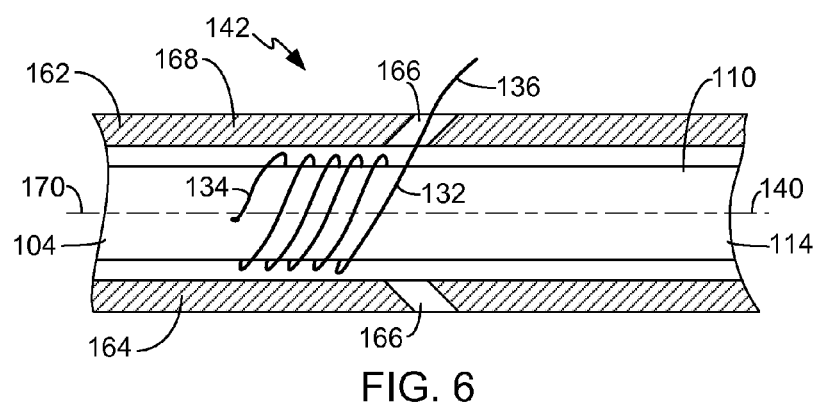
FIG. 6 is a simplified side view of a portion of the electrode lead of FIG. 3 within an introducer sheath shown in cross-section.

FIG. 6 is a simplified side view of the distal end 114 of the electrode lead 104 of FIG. 3 within the distal end 164 of the introducer sheath 162. In accordance with this embodiment, the anchor 142 is deployed by the physician rotating the lead body 110 about the longitudinal axis 170 of the introducer sheath 162, or the longitudinal axis 140 of the lead body 110, relative to the introducer sheath 162. This rotation causes the distal end 136 of the anchor wire 132 to extend through the opening 166 in the sheath wall 168 and into the tissue (not shown) of the patient. The amount of the anchor wire 132 that is fed into the tissue of the patient depends on the amount the lead body 110 is rotated about the axis 170 or the axis 140 relative to the introducer sheath 162. In one embodiment, the distal end 136 of the anchor wire 132 is deployed in a direction that is generally radial to the longitudinal axis 170 or the longitudinal axis 140, as shown in FIG. 6.

After the one or more anchor wires 132 of the anchor 142 are deployed into the tissue of the patient through the rotation of the lead body 110 relative to the introducer sheath 162, the introducer sheath 162 may be removed from the patient without disturbing the anchor wires 132, such as by splitting the introducer sheath into separate halves. The resultant position of the distal end 114 of the electrode lead 104 is in the tissue by the one or more anchor wires 132.

Figure 7:
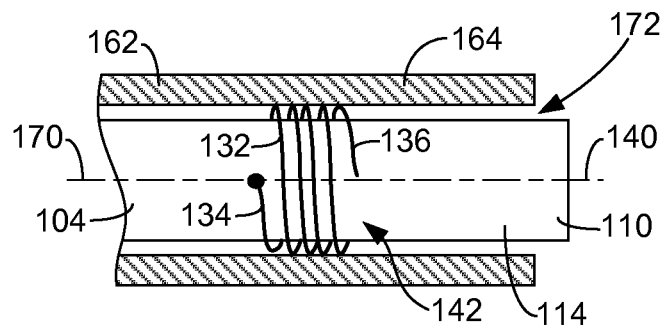
FIG. 7 is a simplified drawing of a portion of an electrode lead comprising an anchor formed in accordance with embodiments of the invention within an introducer sheath shown in cross-section.
Figure 8:
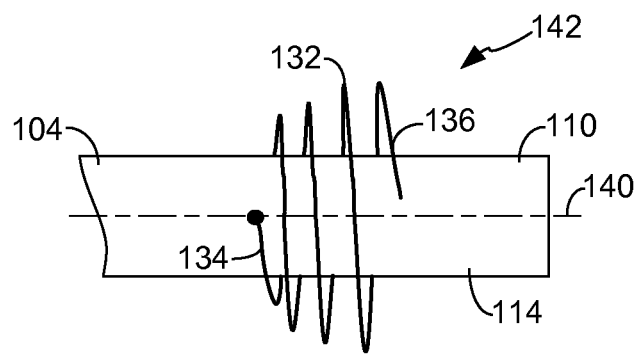
FIGS. 8 and 9 respectively show simplified side and front views of the portion of the electrode lead of FIG. 7 within tissue of a patient after the introducer sheath has been removed.
Figure 9:
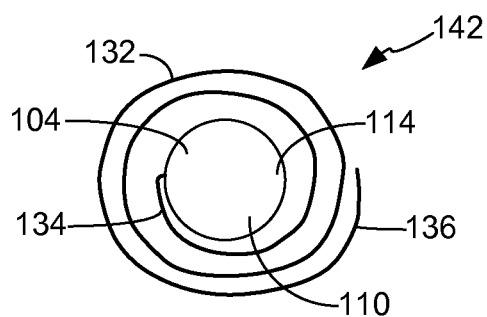

In accordance with another embodiment, the anchor 142 is wound about the distal end 114 of the electrode lead 104 such that it is radially compressed toward the longitudinal axis 140 of the lead body 110 relative to a quiescent state of the anchor wire 132. During the implantation, this radial compression of the at least one anchor wire 132 of the anchor 142 is maintained by the introducer sheath 162, as illustrated in the simplified side view of FIG. 7 with the introducer sheath 162 shown in cross-section. In accordance with this embodiment, the electrode lead 104 is either pushed through an opening 172 at the distal end 164 of the introducer sheath 162, or the introducer sheath 162 is separated into pieces and removed from the patient to expose the distal end 114 of the electrode lead 104 to the tissue of the patient. In response to the removal of the introducer sheath 162, the at least one anchor wire 132 of the anchor 142 expands radially from the longitudinal axis 140 and the lead body 110 toward an expanded quiescent state, as illustrated in the side and front views of FIGS. 8 and 9, respectively. The expansion of the at least one anchor wire 132 into the tissue of the patient secures the position of the distal end 114 of the electrode lead 104 in the tissue of the patient.

Figure 10A:
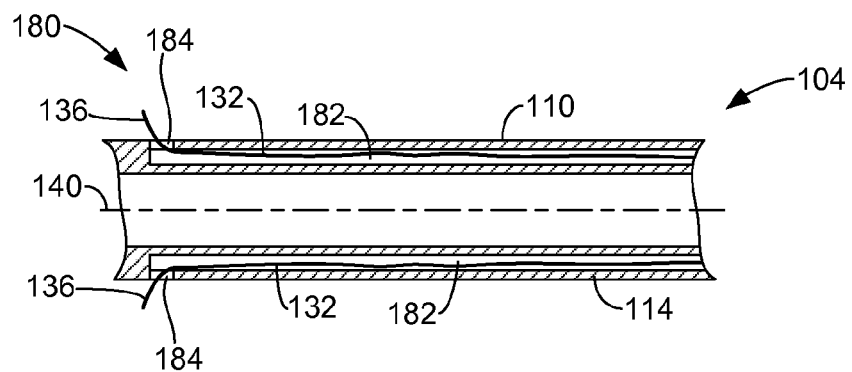
FIGS. 10A-10C are simplified side cross-sectional views of an electrode lead illustrating the deployment of an anchor in accordance with embodiments of the invention.
Figure 10B:
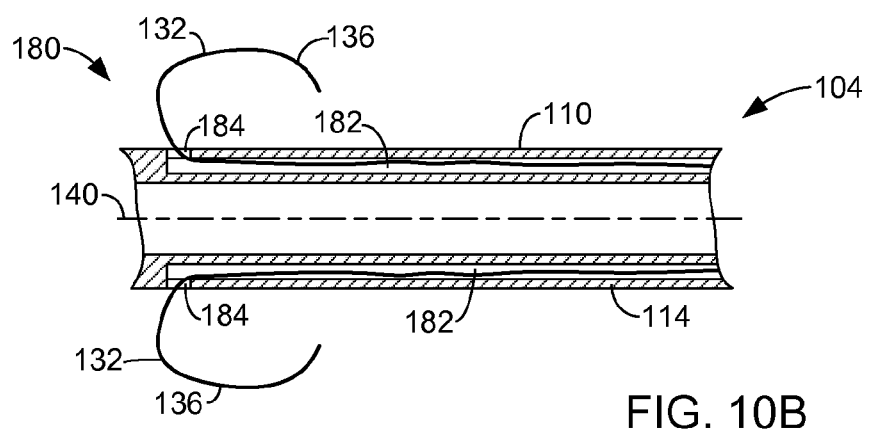
Figure 10C:
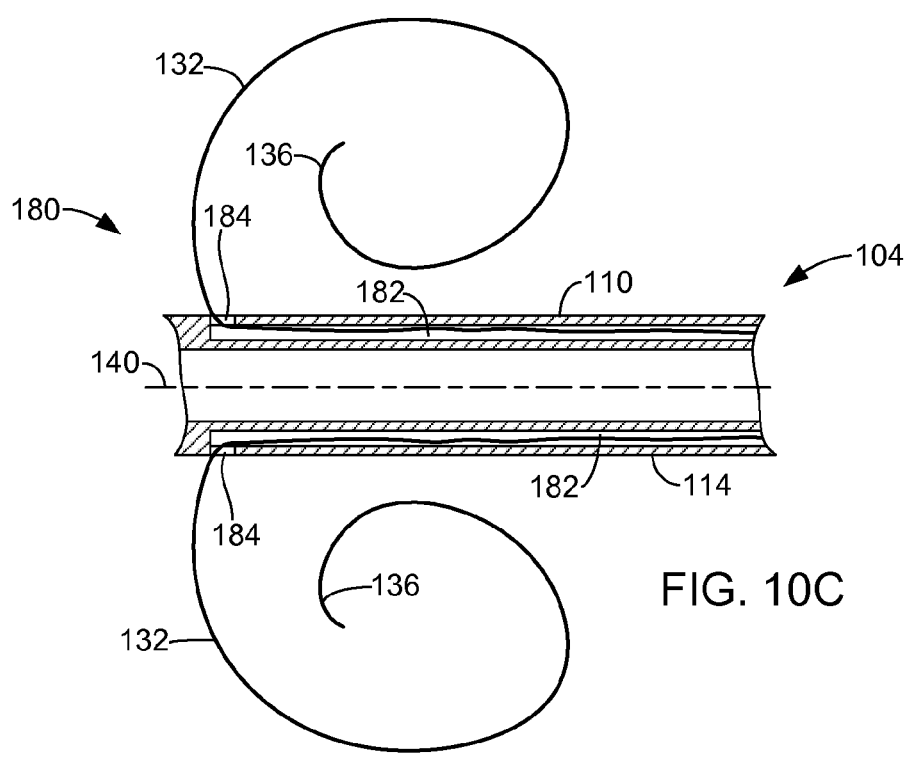

FIGS. 10A-C are side cross-sectional views of a portion of a distal end 114 of an electrode lead 104 illustrating different stages of deployment of an anchor 180 formed in accordance with embodiments of the invention. In one embodiment, the anchor 180 comprises at least one anchor wire 132 that is configured to be fed from within the anchor body 110 into the tissue of the patient after the distal end 114 of the electrode lead 104 is positioned within the targeted tissue using conventional techniques, such as those described above. In one embodiment, one or more lumens 182 are formed in the lead body 110, which guide the one or more anchor wires 132 to openings 184 formed in the lead body 110. The one or more anchor wires 132 have a retracted position, in which the distal ends 136 are contained within the corresponding lumen 182, or are only slightly extended through the openings 184, as shown in FIG. 10A. In one embodiment, the distal end 114 of the electrode lead 104 is fed, such as through an introducer, to the target tissue while the anchor 180 is in the retracted position.

Once the distal end 114 of the electrode lead 104 is positioned as desired within the targeted tissue of the patient, the one or more anchor wires 132 may be deployed from within the lumen 182 and fed into the tissue of the patient, as illustrated in FIGS. 10B and 10C. In one embodiment, the one or more anchor wires 132 are initially fed in a radial direction relative to the longitudinal axis 140 of the lead body 110. The deployment of the one or more anchor wires 132 may be accomplished by the physician using a suitable actuatable member, such as those described below, to which the proximal end of the anchor wires 132 are attached. In one embodiment, as the anchor wires 132 are fed from within the lead body 110, the one or more anchor wires 132 coil within the tissue of the patient, as shown in FIG. 10C. The deployed state (FIG. 10C) of the one or more anchor wires 132 secure the position of the distal end 114 of the electrode lead 104 in the tissue of the patient. When it is desired to remove the electrode lead 104 from the patient, the anchor wires 132 may be retracted within the lumens 182 (FIG. 10A) to reduce damage to the tissue of the patient.

Figure 11A:
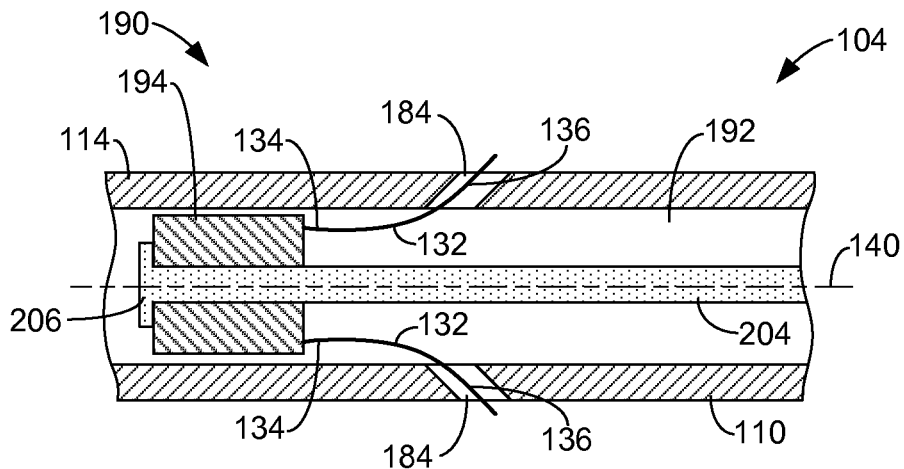
FIGS. 11A and 11B are simplified side cross-sectional views of a portion of an electrode lead illustrating the deployment of an anchor in accordance with embodiments of the invention.
Figure 11B:
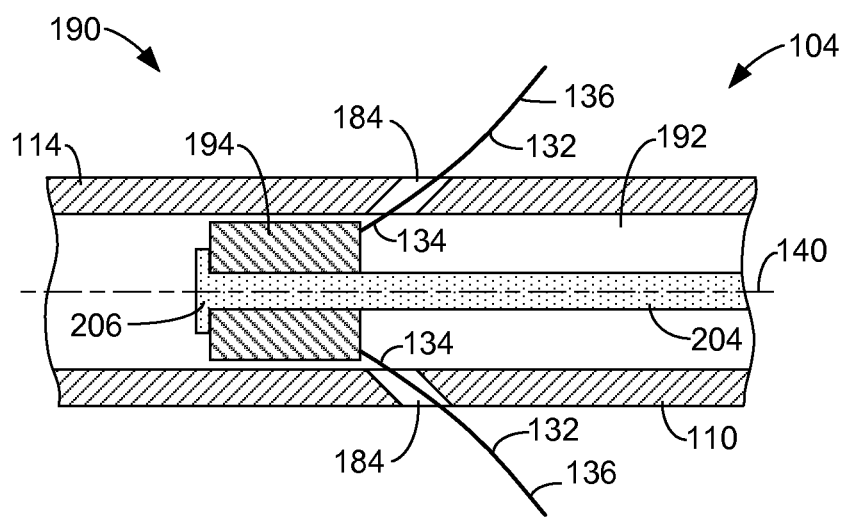

FIGS. 11A and 11B are side cross-sectional views of a portion of a distal end 114 of an electrode lead 104 that includes an anchor 190 formed in accordance with embodiments of the invention. Anchor 190 is similar to anchor 180 (FIGS. 10A-C) in that it includes one or more anchor wires 132 that may be fed from one or more lumens 192 within the anchor body 110. In one embodiment, the proximal ends 134 of the one or more anchor wires are attached to an actuatable member 194. Movement of the actuatable member 194 relative to the lead body 110 along the longitudinal axis 140 transitions the one or more anchor wires 132 between a retracted position (FIG. 11A) and an extended or deployed position (FIG. 11B). As mentioned above with regard to anchor 180, the retracted position of the anchor 190 may position the distal ends 136 of the one or more anchor wires 132 within the lumen 192, or slightly extended through the openings 184 of the lead body 110. The distal end 114 of the electrode lead 110 is positioned within the target tissue using conventional techniques while the anchor 190 is in the retracted position. Once positioned within the targeted tissue of the patient, the actuatable member 194 is moved along the longitudinal axis 140 relative to the lead body 110 to move the distal ends 136 of the one or more anchor wires 132 through the openings 184 and into the tissue of the patient, as illustrated in FIG. 11B. When it is desired to remove the electrode lead 104 from the patient, the anchor wires 132 may be retracted within the lumen 192 (FIG. 11A) to reduce damage to the tissue of the patient.

Figure 12A:
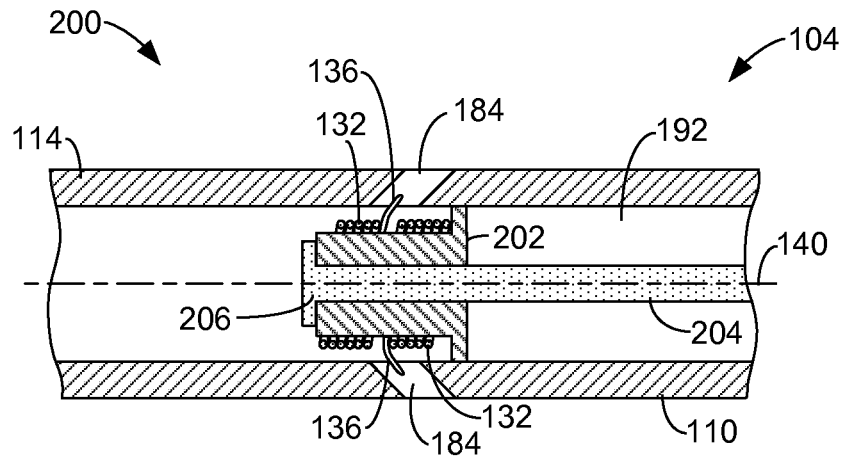
FIGS. 12A and 12B are simplified side cross-sectional views of a portion of an electrode lead illustrating the deployment of an anchor in accordance with embodiments of the invention.
Figure 12B:
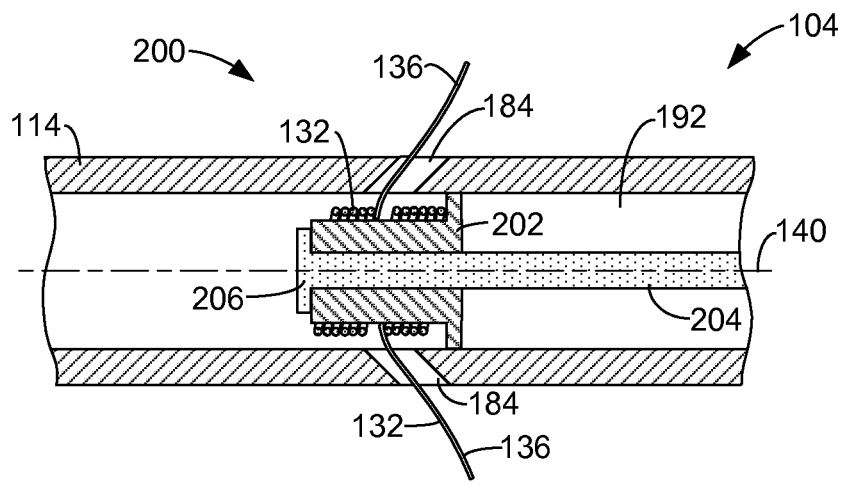

FIGS. 12A and 12B are simplified side cross-sectional views of a portion of a distal end 114 of an electrode lead 104 that includes an anchor 200 formed in accordance with embodiments of the invention. The anchor 200 includes one or more anchor wires 132 that are contained within one or more lumens 192 of the lead body 110. In one embodiment, proximal ends 134 of the one or more anchor wires 132 are attached to an actuatable member 202. Additionally, the one or more anchor wires 132 are wound around the actuatable member 202, which is configured to rotate generally about the longitudinal axis 140 of the lead body 110. Initially, the anchor 200 is placed in a retracted state, in which the distal ends 136 of the one or more anchor wires 132 are located within the lumen 192 or openings 184 of the lead body 110, or are only slightly extended through the openings 184, as shown in FIG. 12A. Once the distal end 114 of the electrode lead 104 is positioned within the targeted tissue of the patient using an introducer or other conventional technique, the actuatable member 202 is rotated generally about the longitudinal axis 140 relative to the lead body 110 by the physician. The distal ends 136 of the one or more anchor wires are fed through the openings 184 of the lead body 110 responsive to the rotation of the actuatable member 202. Thus, the one or more anchor wires 132 move through the openings 184 of the lead body 110 and into the targeted tissue of the patient, as shown in FIG. 12B. This deployed position secures the position of the distal end 114 of the electrode lead 104 in the tissue of the patient. When it is desired to remove the electrode lead 104 from the patient, the anchor wires 132 may be retracted within the lumen 192 (FIG. 12A) to reduce damage to the tissue of the patient.

In one embodiment, a control member 204 may be used by the physician to move the actuatable member 194 (FIGS. 11A-B) along the longitudinal axis 140 relative to the lead body 110, or rotate the actuatable member 202 generally about the longitudinal axis 104 relative to the lead body 110. In one embodiment, the control member 204 is attached to the actuatable member and extends to a proximal end of the lead body 110 where it is accessible by the physician. The physician can slide the control member 204 along the longitudinal axis 140 relative to the lead body 110 to move the anchor 190 between the retracted (FIG. 11A) and deployed (FIG. 11B) positions. Similarly, the physician may rotate the control member 204 to move the anchor 200 between its retracted (FIG. 12A) and deployed (FIG. 12B) positions.

Figure 13:
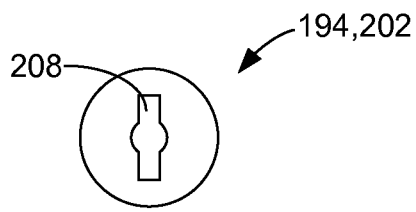
FIG. 13 is a simplified front view of an actuatable member in accordance with embodiments of the invention.

In one embodiment, the control member 204 has a distal end 206 that is removably attachable to the actuatable member 194 or 202. In one embodiment, the actuatable member 194 or 202 includes an aperture 208 that is configured to receive the distal end 206 of the control member 204. In one embodiment, the aperture 208 comprises a keyhole, as shown in the front view provided in FIG. 13. In one embodiment, the distal end 206 is configured to pass through or into the keyhole aperture 208 when angularly aligned with the keyhole aperture 208, and the distal end 206 of the control member 204 is prevented from passing through the keyhole aperture 208 when angularly misaligned with the keyhole aperture 208. This allows the physician to temporarily attach the distal end 206 to the actuatable member 194 or 202, move the actuatable member along the longitudinal axis 140 or rotate the actuatable member about the axis 140, and detach the control member 204 from the actuatable member so that it may be removed from within the lumen 192 of the lead body 110. Other configurations for the control member 204 and the actuatable member may also be used to provide this attachment function.

Figure 14:
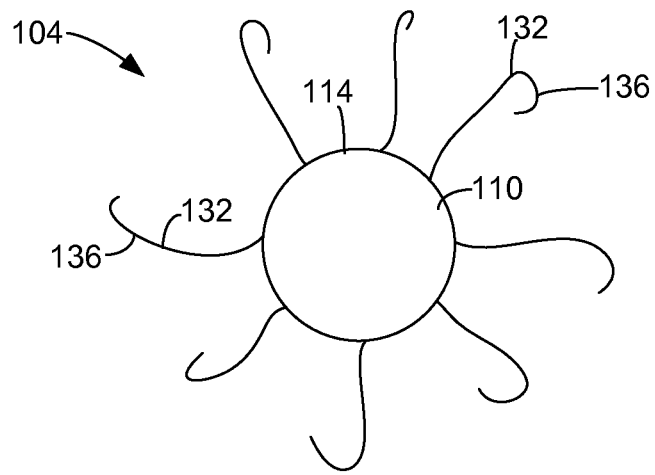
FIGS. 14 and 15 are simplified front views of an electrode lead formed in accordance with embodiments of the invention implanted in tissue of a patient.
Figure 15:
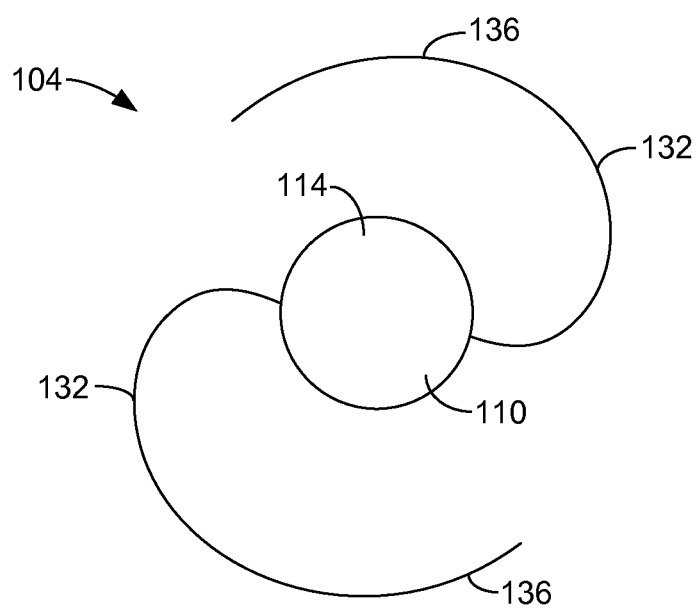

FIGS. 14 and 15 are front views of the distal end 114 of an electrode lead illustrating the deployment of anchor wires 132 in accordance with embodiments of the invention. The depicted anchor wires 132 may be components of anchors 130, 142, 180, 190 or 200, described above. In one embodiment, the anchor wires 132 at least initially extend in a radial direction from the lead body 110 relative to the longitudinal axis 140. In one embodiment, the plurality of anchor wires 132 are angularly displaced about the longitudinal axis. In one embodiment, the distal ends 136 of the anchor wires 132 are configured to coil in a plane that is approximately perpendicular to the longitudinal axis 140. In accordance with another embodiment, the anchor wires 132 are configured to coil in a plane that is approximately parallel to the longitudinal axis 140, as shown in FIG. 10C.

Figure 16:
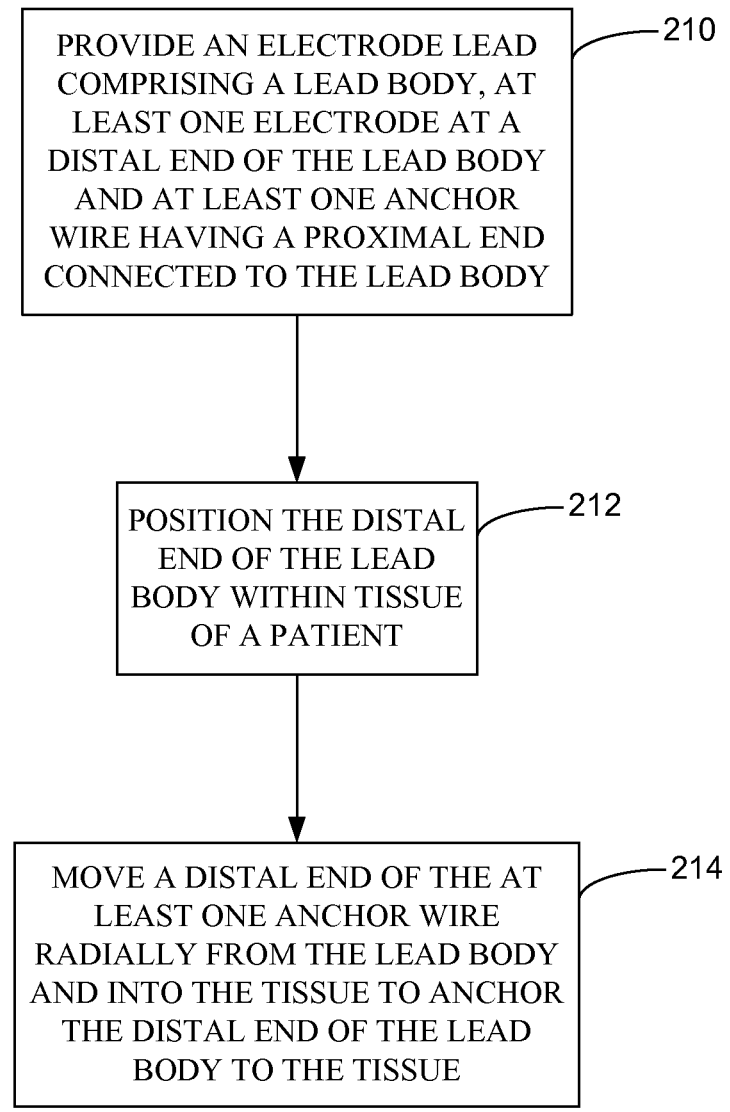
FIG. 16 is a flowchart illustrating a method in accordance with embodiments of the invention.

FIG. 16 is a flowchart illustrating a method in accordance with embodiments of the invention. At 210, an electrode lead 104 is provided comprising a lead body 110, at least one electrode 112 at a distal end 114 of the lead body 110, and at least one anchor wire 132 having a proximal end 134 connected to the lead body 110. In one embodiment, the proximal end 134 is considered to be connected to the lead body 110 through the connection to an actuatable member, such as actuatable member 194 or 202 located within a lumen 192 of the lead body 110, as shown in FIGS. 11A-B and 12A-B.

At 212, the distal end 114 of the lead body 110 is positioned within tissue of a patient. In one embodiment, the distal end 114 is positioned within tissue of the patient using an introducer, as described above. In one embodiment of step 212, an introducer sheath 162 is provided having a sheath wall 168 and a longitudinal axis 170. A distal end 164 of the introducer sheath 162 is then positioned in the targeted tissue of the patient. The distal end 114 of the lead body 110 is then fed into the introducer sheath 162 to position the distal end 114 proximate the distal end 164 of the introducer sheath 162 and the targeted tissue of the patient. In one embodiment, step 212 is performed while the at least one anchor wire 132 is in a retracted position.

At 214, a distal end 136 of the at least one anchor wire 132 is moved radially (i.e., relative to the longitudinal axis 140) from the lead body 110 and into the tissue to anchor the distal end 114 of the lead body 110 to the tissue. That is, the anchor comprising the at least one anchor wire 132 is moved from a retracted position to a deployed position in step 214.

In one embodiment of step 214, a proximal end 134 of the anchor wire 132 is attached to an actuatable member (194 or 202) within a lumen 192 of the lead body, as shown in FIGS. 11A-B and 12A-B. The actuatable member is then moved relative to the lead body 110. In one embodiment, the actuatable member is moved relative to the lead body 110 and the distal end 136 of the at least one anchor wire 132 is moved through an opening 184 in the lead body 110 responsive to moving the actuatable member. In one embodiment, the actuatable member (194) is moved along the longitudinal axis 140 relative to the lead body 110, as shown in FIGS. 11A-B. In accordance with another embodiment, the actuatable member (202) is rotated about the longitudinal axis 140 relative to the lead body 110, as shown in FIGS. 12A-B.

In one embodiment, the at least one anchor wire 132 is a component of anchor 130 (FIG. 2) or anchor 142 (FIG. 3). According to these embodiments, step 214 involves moving the lead body 110 relative to the introducer sheath 162 to deploy the at least one anchor wire 132 into the tissue of the patient. The introducer sheath 162 may then be removed from the tissue without disturbing the deployed anchor wire 132.

When the at least one anchor wire 132 is held in a compressed state by the introducer sheath 162 during the positioning step 212, step 214 of the method is performed by removing the introducer sheath from the tissue. This allows the compressed anchor wire 132 to expand toward its quiescent expanded state and into the tissue of the patient.

Although the present invention has been described with reference to preferred embodiments, workers skilled in the art will recognize that changes may be made in form and detail without departing from the spirit and scope of the invention.

What is claimed is:

1. An electrode lead comprising:
   a lead body having a tubular side wall;
   at least one electrode at a distal end of the lead body;
   an actuatable member within a lumen of the lead body; and
   at least one anchor wire having a proximal end attached to the actuatable member;
   wherein:
     movement of the actuatable member relative to the lead body moves the at least one anchor wire through at least one opening in the sidewall of the lead body; and
     a distal end of the at least one anchor wire moves radially from the lead body relative to a longitudinal axis of the lead body responsive to movement of the actuatable member.

2. The electrode lead of claim 1, wherein:
   the actuatable member is configured to move relative to the lead body along a longitudinal axis of the lead body; and
   the at least one anchor wire is deployed or retracted through the at least one opening responsive to movement of the actuatable member relative to the lead body along the longitudinal axis.

3. The electrode lead of claim 2, further comprising a control member attached to the actuatable member and extending through the lumen of the lead body, wherein movement of the control member drives movement of the actuatable member along the longitudinal axis.

4. The electrode lead of claim 3, wherein the control member has a distal end that is removably attachable to the actuatable member.

5. The electrode lead of claim 4, wherein the actuatable member comprises an aperture that is configured to receive the distal end of the control member.

6. The electrode lead of claim 5, wherein the aperture of the actuatable member comprises a keyhole, wherein the distal end of the control member may pass through the keyhole when angularly aligned with the keyhole, and the distal end of the control member is prevented from passing through the keyhole when angularly misaligned with the keyhole.

7. The electrode lead of claim 1, wherein:
   the actuatable member is configured to rotate relative to the lead body about a longitudinal axis of the lead body; and
   the at least one anchor wire is extended or retracted through the at least one opening responsive to rotation of the actuatable member about the longitudinal axis relative to the lead body.

8. The electrode lead of claim 7, wherein the at least one anchor wire is wound around the actuatable member.

9. A method comprising:
   providing an electrode lead comprising a lead body, at least one electrode at a distal end of the lead body and at least one anchor wire having a proximal end connected to the lead body;
   positioning the distal end of the lead body within tissue of a patient;
   moving a distal end of the at least one anchor wire radially from the lead body relative to a longitudinal axis of the lead body; and
   piercing the tissue with the distal end of the anchor wire responsive to moving a distal end to anchor the distal end of the lead body to the tissue.

10. The method of claim 9, wherein:
    providing an electrode lead further comprises providing an actuatable member within a lumen of the lead body, wherein the proximal end of the at least one anchor wire is attached to the actuatable member; and
    moving a distal end of the at least one anchor wire comprises:
      moving the actuatable member relative to the lead body; and
      moving the distal end of the at least one anchor wire through an opening in a tubular sidewall of the lead body responsive to moving the actuatable member.

11. The method of claim 10, wherein moving the actuatable member relative to the lead body comprises moving the actuatable member along a longitudinal axis of the lead body relative to the lead body.

12. The method of claim 10, wherein moving the actuatable member relative to the lead body comprises rotating the actuatable member about a longitudinal axis of the lead body relative to the lead body.

13. The method of claim 10, wherein positioning the distal end of the lead body within tissue of a patient comprises:
    providing an introducer sheath having a sheath wall and a longitudinal axis;
    positioning a distal end of the sheath in the tissue of the patient; and
    feeding the distal end of the lead body into the introducer sheath.

14. The method of claim 13, wherein moving a distal end of the at least one anchor wire comprises:
    moving the distal end of the lead body relative to the introducer sheath; and
    moving the distal end of the at least one anchor wire through at least one opening in the sheath wall and into the tissue responsive to moving the distal end of the lead body.

15. The method of claim 14, wherein moving the distal end of the lead body comprises moving the distal end of the lead body along the longitudinal axis of the introducer sheath relative to the introducer sheath.

16. The method claim 14, wherein moving the distal end of the lead body comprises rotating the distal end of the lead body about the longitudinal axis of the introducer sheath relative to the introducer sheath.

* * * * *